(12) United States Patent
Breton

(10) Patent No.: US 7,125,559 B2
(45) Date of Patent: *Oct. 24, 2006

(54) COSMETIC OR DERMATOLOGICAL COMPOSITION COMPRISING A COMBINATION OF AN ELASTASE INHIBITOR OF THE N-ACYLAMINOAMIDE FAMILY AND AT LEAST ONE MYORELAXING AGENT

(75) Inventor: Lionel Breton, Versailles (FR)

(73) Assignee: L'Oreal, Paris (FR)

( * ) Notice: Subject to any disclaimer, the term of this patent is extended or adjusted under 35 U.S.C. 154(b) by 241 days.

This patent is subject to a terminal disclaimer.

(21) Appl. No.: 10/179,984

(22) Filed: Jun. 26, 2002

(65) Prior Publication Data

US 2003/0064085 A1    Apr. 3, 2003

(30) Foreign Application Priority Data

Jun. 26, 2001 (FR) .................................. 01 08436

(51) Int. Cl.
*A61K 31/165* (2006.01)

(52) U.S. Cl. .................... 424/401; 514/617; 514/619

(58) Field of Classification Search ............... 424/401; 514/617, 619
See application file for complete search history.

(56) References Cited

U.S. PATENT DOCUMENTS 5,234,909 A    8/1993 Phiippe

| 6,335,368 B1 * | 1/2002 | Liviero et al. ............ 514/561 |
| 6,344,461 B1 * | 2/2002 | Breton et al. ............ 514/277 |
| 6,572,848 B1 * | 6/2003 | Breton et al. ........... 424/78.02 |
| 2003/0044438 A1 * | 3/2003 | Breton et al. ............ 424/401 |
| 2003/0072732 A1 * | 4/2003 | Breton et al. ........... 424/70.22 |
| 2003/0152596 A1 * | 8/2003 | Breton et al. ............ 424/401 |
| 2003/0152600 A1 * | 8/2003 | Dalko et al. ............. 424/401 |

FOREIGN PATENT DOCUMENTS

| EP | 0 704 210 | 4/1996 |
| EP | 1 053 745 | 11/2000 |
| EP | 1 088 548 | 4/2001 |
| FR | 2 810 033 | 12/2001 |
| JP | 2000-178163 | * 6/2000 |
| WO | WO 00/12467 | 3/2000 |

OTHER PUBLICATIONS

Masayuki Nakamura et al.; "A Two-Step, One-Pot Synthesis of Diverse N-Pyruvoyl Amino Acid Derivatives Using the Ugi Reaction"; Bioorganic & Medicinal Chemistry Letter 10 (2000) 2807-2810.

* cited by examiner

*Primary Examiner*—San-Ming Hui
(74) *Attorney, Agent, or Firm*—Oblon, Spivak, McClelland, Maier & Neustadt, P.C.

(57) ABSTRACT

Cosmetic or dermatological composition characterized in that it comprises a combination of an elastase inhibitor of the N-acylaminoamide family and at least one myorelaxing agent.

28 Claims, No Drawings

COSMETIC OR DERMATOLOGICAL COMPOSITION COMPRISING A COMBINATION OF AN ELASTASE INHIBITOR OF THE N-ACYLAMINOAMIDE FAMILY AND AT LEAST ONE MYORELAXING AGENT

The present invention relates to the field of cosmetic or dermatological compositions. It relates to novel cosmetic or dermatological compositions comprising a combination of an inhibitor of elastase of the N-acylaminoamide family and at least one myorelaxing agent. This composition is preferably designed to improve the cutaneous signs of ageing and/or photo-ageing, and in particular wrinkles, by retarding the adverse changes of the conjunctive tissue and by improving the functional state of the skin while conferring on it a myorelaxing action.

The human skin is constituted of two compartments, namely a superficial compartment, the epidermis, and a deep compartment, the dermis.

The natural human epidermis is composed principally of three types of cells which are the keratinocytes, very largely predominant, the melanocytes and the cells of Langerhans. Each of these cell types contributes as a result of its intrinsic functions to the essential role played in the organism by the skin.

The dermis provides the epidermis with a solid support. It is also its nutritive element. It is constituted mainly of fibroblasts and of an extracellular matrix itself composed principally of collagen, elastin and a substance called fundamental substance, compounds synthesized by the fibroblasts. Leukocytes, mastocytes or also tissue macrophages are also found there. Blood vessels and nerve fibres also pass through it.

Moreover, it is known that the muscles of the facial skin are under the control of the motor afferent nerves of the facial nerve. On the other hand, a subpopulation of fibroblasts of the dorm (that are called myofibroblasts) possess certain characteristics in common with muscle tissue. In certain pathological and therapeutic situations the nervous control of the entire muscular tissue of the face plays a major role in the appearance of facial wrinkles. Thus, in the attacks of the facial nerve, in which the transmission of the nervous influx is interrupted and/or diminished, one witnesses a paralysis of the facial muscles in the field of innervation. This facial paralysis results in, among other clinical signs, an attenuation, even a disappearance of the wrinkles. Furthermore, it has been shown that the botulin toxin, originally used to treat spasms, can act on the states of muscular spasticity (see A. Blitzer et al., Arch. Otolaryngol. Head Neck Surg., 1993, 199, pages 1018 to 1022) and on the wrinkles of the glabella which are the wrinkles between the eyebrows (see J. D. Carruters et al., J. Dermatol. Surg. Oncol., 1992, 18, pages 17 to 21). Consequently, it is thus possible to act by means of a pharmacological action on the neuromuscular component of the wrinkles.

In the peripheral nervous system, the junction between the nerve and a striated muscle is constituted by the neuromuscular plate, upstream from which is found the afferent nervous pathway called the motoneurone. Furthermore, the cell membranes of each nerve fibre but also muscle cells comprise many ion channels and in particular calcium channels and chloride channels, capable of letting pass through $Ca^{++}$ or $Cl^-$, respectively, pass through in a controlled manner.

In the muscle cells, the final messenger of muscle contraction is also calcium, the increase of which in the cytoplasm of the myocyte makes possible the activation of the contractile machinery. It is generally accepted that during the contraction phase the thin filaments of actin slide between the thick filaments of myosin thus leading to the shortening of the sarcomers and consequently to a contractile movement of the cell and, overall, of the fibre.

In the relaxed state, actin is not accessible to the myosin bridges because it is associated with another protein complex constituted by troponin and tropomyosin.

When calcium is bound to the troponin-tropomyosin complex, the actin molecules become accessible and the contractile phenomenon can then start.

It consists of an ATPase reaction which produces the energy for the recycling of the bridges.

The role of $Ca^{2+}$ at the level of the contractile proteins of the striated muscles is an activating (disinhibitory) role of ATPase activity.

The relaxing of striated muscle occurs when the transverse tubules and the cell membrane are repolarised, this makes it possible for the intra-cytoplasmic cell concentration of $Ca^{2+}$ to return to a value of $10^{-7}$, lower than the activation threshold of the intracellular enzymes such as ATPase (activation threshold which is about 1 to 2 logarithms of concentration higher).

Calcium is not an activator per se but it becomes so after the formation of a complex with calmodulin, a small protein (18,000 daltons). This contraction-relaxation cycle is due to the variations in the concentration of the cytoplasmic calcium from $10^{-7}$ (inactive) to $10^{-5}$ M (active).

The regulation of the intracellular concentration of $Ca^{2+}$ is only possible because the cytoplasmic effluxes of calcium correct the cytoplasmic influxes. The intra-cytoplasmic $Ca^{++}$ exchanges occur either via-à-vis intracellular reserve vesicles or vis-à-vis the exterior of the cell. In both cases, the $Ca^{++}$ is not available in the cytoplasm. These exchanges can only be maintained by an expulsion of the intracellular cytoplasmic calcium by one or more so-called active mechanisms, capable of overcoming the electrochemical potential gradient mentioned above.

Two types of mechanisms can intervene: a calcium pump which actively expels the cations at the expense of the hydrolysis of ATP and a movement of $Ca^{2+}$ coupled with a movement of $Na^+$. In most cells, the ATP-dependent calcium pump operates more efficiently in the presence of calmodulin which Increases its affinity.

In order to better describe the permeability changes to calcium, it is currently usual to consider that this permeability corresponds to the opening of membrane calcium channels, channels operated by variations of the membrane potential (VOC) or the activation of membrane receptors (ROC). At present, three VOC types of calcium channel (L, N, T) have been identified. On the other hand, it is probable that these calcium channels possess tissue specificities.

In 1965, T. Godfraind demonstrated that the permeability of the membrane to calcium could be inhibited by pharmacological agents, and this would constitute the common mechanism by which $Ca^{2+}$ antagonists act.

Independently of the $Ca^{2+}$ blocking agents, the agents opening chloride ($Cl^-$) channels such as those described in the patent application EP 0704210 also constitute myorelaxants usable according to the invention. The chloride channel opening compounds constitute "chloride channel agonists" in the context of the invention.

It will therefore be understood from the foregoing that the contraction or hypercontraction of certain facial muscles, or of certain contractile cells of the dermis such as the myofibroblasts, results in the appearance of wrinkles.

This muscular activation is itself induced by different mechanisms causing in particular ion exchanges of $Cl^-$, $Ca^{2+}$ and intracellular calcium.

The applicant has now discovered after many clinical tests that the contractile muscle fibre, which is under the direct control of the neuromotor influx, plays an essential role in the formation of wrinkles and that the modulation of the neuro-motor influx and the control of the contraction of the muscle fibres play an essential role in the formation of wrinkles. Thus the modulation of motor contraction attenuates not only the wrinkles but also the skin creases and thus has a "smoothing" effect on the cutaneous microrelief. The applicant has also found that the cutaneous and subcutaneous tissues comprise calcium channels, a fact which hitherto has not been considered.

Furthermore, in the long-term, the sum of the cutaneous micro-stresses, generated for example by ageing or by prolonged exposure to the UV (in this case, it is called photo-ageing)can lead to a more or less accelerated loss of the natural elasticity of the skin. The network formed by the elastic fibres of the underlying conjunctive tissue and the extracellular spaces can then be progressively disrupted. This is followed by accelerated ageing of the skin (wrinkled and/or less supple skin) via the impairment of the dermal elastic network as well as an accentuation of the wrinkles (deeper wrinkles).

When stressed, the keratinocytes release biological mediators (called chemo-attractant factors) which possess the capacity to attract certain inflammatory cells of the blood compartment towards the cutaneous tissue. These cells are responsible for the genesis, then the maintenance, of a local irritation during the state of ageing.

Of the chemo-attractant factors which can be produced by the "stressed" keratinocytes, interleukin 8 (IL-8) is more specifically responsible for the recruitment of the polymorphonuclear neutrophils. These cells infiltrating the irritated or aggressed areas then release enzymes including the leukocyte elastase and other proteases (metalloproteinases, serine proteases etc. . . . )

Under the action of elastase, the elastin fibres of extracellular support of the conjunctive tissue are degraded. In synergy with cathepsin G, the leukocyte elastase can even dissociate the integrity of the epidermis by enlarging the Interkeratinocyte intercellular spaces (Ludolph-Hauser et al. Exp. Dermatol. 1999 8 (1) 46–52). The leukocyte elastase has recently been held responsible for the maintenance of scabs and the occurrence of venous ulcers of the legs owing to its ability to degrade fibronectin (Herrick S et al. Lab. Invest. 1997 (3) 281–288). The sum of the localised degradative micro-stresses (subsequent for example to prolonged exposure to the sun) can result in the long term in an accelerated loss of the natural elasticity of the skin. The network of elastic fibres of the underlying conjunctive tissue and the extracellular spaces is then progressively disrupted. This accelerated degradation can proceed together with the process of normal ageing of the skin which is characterized by a greater sensitivity of the elastin fibres to the action of elastase (Stadler R & Orfanos C E Arch. Dermatol. Res. 1978 262 (1) 97–111.

It is known in the state of the art that molecules capable of retarding the degradative activity of the elastic fibres of the intercellular spaces can be introduced into the cutaneous tissue.

The object of the present invention is to suggest a solution for these different problems, and in particular to suggest novel compounds capable of being used as cosmetics or pharmaceutical agents for limiting the ageing of the skin, whether chronobiological or photo-induced, and in particular ageing generated by a diminution of the elasticity of the skin and/or by degradation of the collagen in the structure of the tissues.

The technical solution according to the invention consists of providing, in addition to the regulatory element downstream from the elastase activity (i.e. the N-acylaminoamide derivative, the inhibitor of the enzymatic activity of leukocyte elastase) one or more active compounds capable of also regulating the cutaneous myofibrillar component.

Consequently, the object of the invention is a cosmetic or dermatological composition characterized in that it comprises a combination between an inhibitor of elastase of the N-acylaminoamide family and at least one myorelaxing agent.

Preferably, the myorelaxing agent is selected from a calcium channel inhibitor and/or a chloride channel agonist.

Another object of the invention consists in a cosmetic treatment procedure of the skin of the body or face, including the scalp, in which a cosmetic composition such as defined above is applied to the skin.

It has in fact been observed that the compounds of formula (I) possess an inhibitory effect on the activity of the elastases and that they can hence be used to limit and/or control the degradation of the elastin fibres.

It follows from that that they can be used in or for the preparation of a composition, the compounds or the composition being designed to treat the cutaneous signs of ageing preventively and/or curatively.

The novel combination of the N-acylaminoamide compounds with at least one myorelaxing agent makes it possible to significantly reinforce the anti-ageing effect of the matrix tissue by the application of a relaxing effect on the cutaneous tissue and/or subcutaneous tissue.

Thus, the combined use in a cosmetic composition of an elastase inhibitor of the N-acylaminoamide family and a myorelaxing agent, preferably of the $Ca^{++}$ antagonist and/or $Cl^-$ channel opening type contributes to a greater anti-wrinkle activity via a protective and regulatory action on the supporting tissue of the skin and via a myorelaxing activity on all of the myofibrils of the dermis and/or hypodermis.

According to the invention, the regulatory element of the elastase activity is combined with one or more active compounds capable of regulating the cutaneous myofibrillar component.

The composition obtained is intended for the treatment of ageing disorders and/or to be more specifically designed to treat all of the skin disorders associated with too great a proliferation of cutaneous bacteria and/or yeasts (*P. Ovale, P. Acnes, A. Aureus*).

Preferably, this novel combination is used in care and/or hygiene cosmetic preparations of the areas exposed to the sun (scalp, body, face, lips), in care and/or hygiene cosmetic preparations of ulcerated areas, in toothpastes or mouth washes and, generally, in all of the so-called "anti-skin ageing" cosmetic preparations which have as objective the retardation of the chronobiological destructuration of the supporting tissue and of the architecture of the cutaneous matrix elements. More particularly, this combination should be reserved for comedone- and acne-infected skins, as well as for skins having being subject to moderate effects such as scratches, abrasions, first degree burns or higher degree burns but undergoing resorption.

Without wanting to be bound by any theory, the applicant considers that the fact to supply at the level of the keratinocytes of the superficial layers of the skin compounds capable of retarding the degradative activity of the elastic fibres of the intercellular spaces may make it possible to diminish this phenomenon of accelerated skin ageing, due to superficial cutaneous stresses and that the combination of these compounds with an calcium channel inhibitor or a chloride channel agonist considerably reinforces their effects.

Preferred N:acylamino-amide Compounds

The compounds susceptible to being used in the present invention thus conform to the following formula (I):

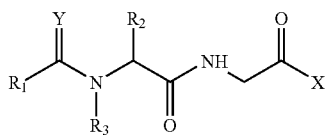

In which:
the radical Y represents O or S.
the radical R1 represents:
(i) a hydrogen atom
(ii) a hydrocarbon radical, linear, branched or cyclic, saturated or unsaturated, containing 1 to 18 carbon atoms, optionally substituted by 1 to 5 groups, identical or different, selected from
—OH; —OR; —O—COR; —SH; —SR; —S—COR; —NH2; —NHR; —NRR'; —NH—COR; -Hal (halogen); —CN; —COOR; —COR; —P(O)—(OR)2; —SO2—OR;

with R and R' representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH2; —NHR"; —NH—COR"; -Hal (halogen); —CN; —COOR"; —COR"; with R" representing independently a hydrocarbon radical, linear, branched or cyclic, saturated or unsaturated, containing 1 to 6 carbon atoms, optionally halogenated, even perhalogenated;
(iii) a radical selected from the radicals —OR; —NH2; —NHR; —NRR'; —NH—COR; —COOR; —COR;

with R and R' representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH2; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;
the radical R2 represents a hydrocarbon radical, linear, branched or cyclic saturated or unsaturated, containing 1 to 18 carbon atoms, optionally substituted by 1 to 5 groups, identical or different, selected from
—OH; —OR; —O—COR; —SH; —SR; —S—COR; —NH2; —NHR; —NRR'; —NH—COR; -Hal (halogen); —CN; —COOR; —COR;

with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from
—OH; —OR"; —O—COR"; —SH; —SR"; —S—COR"; —NH2; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;
the radical R3 represents a radical selected from those of formula (II) or (III)

$$-A-C_6H_{(5-y)}-B_y$$  I.

$$-C_8H_{(5-y')}-B_{y'}$$  II.

in which:
y is an integer included between 0 and 5, and y' is an integer included between 1 and 5;
A is a divalent hydrocarbon radical, linear, branched or cyclic, saturated or unsaturated, containing 1 to 18 carbon atoms, optionally substituted by 1 to 5 groups, identical or different, selected from
—OH; —OR; —O—COR; —SH; —SR; —S—COR; —NH2; —NHR; —NRR'; —NH—COR; -Hal (halogen, even perhalogen); —CN; —COOR; —COR; —NO2; —SO2—OR;

with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S In the ring, and/or may be substituted by 1 to 5 groups, identical or different, selected from
—OH; —OR'; —O—COR"; —SH; —SR"; —S—COR"; —NH2; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;
B is a hydrocarbon radical, linear, branched or cyclic, saturated or unsaturated, containing 1 to 18 carbon atoms, optionally substituted by 1 to 5 groups, identical or different, selected from —OH; —OR; —O—COR; —SH; —SR; —S—COR; —NH$_2$; —NHR; —NRR'; —NH—COR; -Hal (halogen, even perhalogen); —CN; —COOR; —COR; —NO$_2$; —SO$_2$—OR;

with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH$_2$; —NHR"; —NH—COR"; -Hal (halogen): —CN; —COOR"; —COR": with R" representing a hydrocarbon radical, linear, branched or cyclic, saturated or unsaturated, containing 1 to 6 carbon atoms, optionally halogenated, even perhalogenated;

the radical X represents a radical selected from —OH; —OR$_4$, —NH$_2$, —NHR$_4$, NR$_4$R$_6$, —SR$_4$, —COOR$_4$; —COR$_4$;

With R$_4$ and R$_5$ each representing independently a hydrocarbon radical, linear, branched or cyclic, saturated or unsaturated, containing 1 to 6 carbon atoms, optionally substituted by 1 to 5 groups, identical or different, selected from —OH; —OR; —O—COR; —SH; —SR; —S—COR; —NH$_2$; —NHR; —NRR'; —NH—COR; -Hal (halogen, even perhalogen); —CN; —COOR; —COR;

with R and R' each representing independently a hydrocarbon radical, linear, branched or cyclic, saturated or unsaturated, containing 1 to 6 carbon atoms, optionally halogenated, even perhalogenated, the said R and R' radicals being capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;

the said R$_4$ and R$_5$ radicals being capable of forming together with N a 5- or 6-membered carbon ring that may include in addition at least one heteroatom selected from O, N and/or S in the ring, and/or may be substituted by 1 to 5 groups, identical or different, selected from —OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, even perhalogenated;

Also included in this definition are the mineral or organic acid salts of said compounds as well as their optical isomers, in isolated form or as a racemic mixture.

By hydrocarbon radical, linear, cyclic or branched, is meant in particular the radicals of the alkyl, aryl, aralkyl, alkylaryl, alkenyl and alkynyl type.

The group $C_6H_5$ present in the radical R3 must be understood as a cyclic aromatic group.

Preferably, the radical Y represents oxygen.

Preferably, the radical R1 represents hydrogen or a hydrocarbon radical, linear or branched, saturated or unsaturated, containing 1 to 12, and in particular 1, 2, 3, 4, 5 or 6 carbon atoms, optionally substituted.

In particular, the substituents may be selected from —OH, —OR and/or —P(O)—(OR)$_2$ with R representing a hydrocarbon radical, linear, branched or cyclic, saturated or unsaturated, containing 1 to 6 carbon atoms, optionally halogenated, even perhalogenated.

Preferably, the radical R1 represents a methyl, ethyl, propyl or isopropyl radical, optionally substituted by a —OH or —P(O)—(OR)$_2$ group with R representing methyl, ethyl, propyl or isopropyl.

Preferably, the radical R2 represents a hydrocarbon radical, linear or branched, saturated or unsaturated, containing 1 to 12, and in particular 1, 2, 3, 4, 5 or 6 carbon atoms, optionally substituted.

In particular, the substituents may be selected from —OH and —OR with R representing a hydrocarbon radical, linear, branched or cyclic, saturated or unsaturated, containing 1 to 6 carbon atoms, optionally halogenated, even perhalogenated.

Preferably, the radical R2 represents a methyl, ethyl, propyl, isopropyl, n-butyl, tert.butyl or isobutyl radical.

Preferably, the radical R3 represents a radical of formula —C$_6$H$_{(5-y')}$—B$_{y'}$', for which y'=1, 2 or 3; or a radical of formula —A—C$_6$H$_{(5-y)}$—B$_y$, for which y=0, 1 or 2. Preferably, A is a divalent hydrocarbon radical, linear or branched, saturated or unsaturated, containing 1 to 12 carbon atoms, optionally substituted. The substituents of A are preferably selected from -Hal (halogen, even perhalogen); —CN; —COOR; —NO$_2$; —SO$_2$—OR; with R representing a hydrocarbon radical, linear, branched or cyclic, saturated or unsaturated, containing 1 to 6 carbon atoms, optionally halogenated, even perhalogenated.

Preferably, B is a hydrocarbon radical, linear or branched, saturated or unsaturated, containing 1 to 12 carbon atoms, optionally substituted.

The substituents of B are preferably selected from -Hal (halogen, even perhalogen); —CN; —COOR; —NO$_2$; —SO$_2$—OR; with R representing a hydrocarbon radical, linear, branched or cyclic, saturated or unsaturated, containing 1 to 6 carbon atoms, optionally halogenated, even perhalogenated.

Preferably, the radical R3 represents a group selected from one of the following formulae:

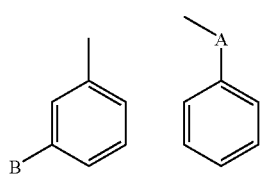

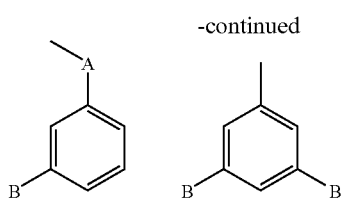

in which A and B have the above meanings.

In particular, the divalent radical A may be methylene, ethylene, propylene.

The radical B is preferably a methyl, ethyl, propyl or isopropyl radical, substituted by one or more halogens, in particular chlorine, bromine, iodine or fluorine, and preferably completely halogenated (perhalogenated), such as perfluorinated. Particular mention may be made of the perfluoromethyl radical (—CF3) as very particularly preferred.

Preferably, the radical X represents a radical selected from —OH or —OR$_4$ with R$_4$ representing a hydrocarbon radical, linear, cyclic or branched, saturated or unsaturated, containing 1 to 6 carbon atoms, optionally substituted. The substituents may be selected from —OH and —OR with R representing a hydrocarbon radical, linear, branched or cyclic, saturated or unsaturated, containing 1 to 6 carbon atoms, optionally halogenated, even perhalogenated. Preferably, the radical X represents a radical selected from —OH, —OCH$_3$, —OC$_2$H$_5$, —O—C$_3$H$_7$ or —OC$_4$H$_9$.

Of the particularly preferred compounds mention may be made of:

{2-[acetyl-(3-trifluoromethyl-phenyl)-amino]-3-methyl-butyrylamino}acetic acid

{2-[acetyl-(3-trifluoromethyl-phenyl)-amino]-3-methyl-butyrylamino}ethyl acetate

[2-(acetyl-benzyl-amino)-3-methyl-butyrylamino]acetic acid

[2-(acetyl-benzyl-amino)-3-methyl-butyrylamino]ethyl acetate (2-{benzyl-[(diethoxy-phosphoryl)-acetyl]-amino}-3-methyl-butyrylamino) ethyl acetate.

The compounds according to the invention can be easily prepared by the specialist skilled in the art on the basis of his general knowledge. In particular, it is possible to react a carboxylic acid, an aldehyde, an amino compound and an isonitrile according to the Ugi reaction.

It is clearly understood that during the synthesis of the compounds according to the invention and as a function of the nature of the different radicals present in the starting compounds, the specialist will take care to protect certain substituents in order that they do not reaction in the course of the reactions.

The quantity of compound to be used in the compositions according to the invention can easily be determined by the specialist skilled in the art as a function of the nature of the compound used, the person to be treated and/or the effect desired. Generally, this quantity may be comprised between 0.00001 and 20% by weight of the total weight of the composition, in particular between 0.001 and 10% by weight and preferably between 0.05 and 5% by weight.

The compounds of formula (I) may in particular be used in a composition which comprises a physiologically acceptable medium, in particular in a cosmetic or pharmaceutical composition which hence comprises moreover a cosmetically or pharmaceutically acceptable medium.

The physiologically acceptable medium in which the compounds according to the invention may be used as well as its constituents, their quantity, the formulation of the composition and its method of preparation can be chosen by the specialist skilled in the art on the basis of his general knowledge as a function of the type of composition desired.

Generally speaking, this medium can be anhydrous or aqueous. Thus it may comprise an aqueous phase and/or a fatty phase.

PREFERRED MYORELAXING AGENTS ACCORDING TO THE INVENTION

Calcium Channel Inhibitors

In order that a substance be recognized as a calcium channel inhibitor, otherwise called in the text calcium inhibitor, it must be able to diminish the intracellular calcium concentration or diminish the binding of calcium to the intracellular proteins like for example calmodulin, such as is described in particular for example by Galizzi, J. P. et al. J. Biol. Chem. 1987, 262, p. 6947 or Y. Okamiya et al., Eur. J. Pharmacol. 1991, 205, p. 49 or J. A. Wagner et al., J. Neurosci. 1988, 8, p. 3354 or H. R. Lee et al., Life Sci. 1984, 35, p. 721 or Schoemaker H. et Lauger S., Eur. J. Pharmacol. 1985 111, p. 273 oor also I. J. Reynolds et al., J. Pharmacol. Exp. Ther. 1986, 237, p. 731.

A substance is recognized as a relaxant in the sense of the invention when it shows a relaxation effect on a contracted muscular tissue and/or shows an inhibitory effect in an experimental model of a myoneural junction (motor end plate) in particular in the model described by W. Steinbrecher in: Electrodes for stimulation and bioelectric potential recording, Ed. Biomerstechnich, 1988, pages 96–98.

The efficacious quantity of inhibitor of at least one calcium channel usable according to the invention is obviously a function of the effect desired and can thus vary to a large extent.

In order to give an order of magnitude it is possible to use according to the invention an inhibitor of at least one calcium channel in a quantity representing from 0.0001% to 10% of the total weight of the composition and preferably in a quantity representing from 0.001% to 5% of the total weight of the composition.

Of the calcium antagonists, it is necessary to consider two classes of active compounds, the agents active on the plasma membrane and the agents active in the interior of the cell, respectively.

1) Agents Active on the Plasma Membrane, Inhibitors of Calcium Entry:

The calcium channel inhibitors usable according to the invention are agents active on the plasma membrane, complexing the calcium and/or inhibitors of the entry of calcium such as the phenylalkylamines like for example verapamil, anipamil, gallopamil, devapamil, falipamil, tiapamil, dihydropyridines like for example nifedipine, amiodipine, dazodipine, felodipine, isradipine, nicardipine, nimodipine, nisoldipine, nitrendipine, ryosidine, benzothiazepine like for example diltiazem, diphenylpiperazines like for example cinnarizine, flunarizine, alverine and/or their inorganic or organic salts and/or their chemical derivatives, manganese and its organic and/or inorganic salts.

2) Agents Active at the Interior of the Cell (Release of Intracellular Reserves of Ca$^{2+}$ or then Inhibition of the Formation of the Ca$^{2+}$ Calmodulin Complex), The preferred agents active at the interior of the cell according to the invention are those involved in the release of the intracellular reserves of calcium or then in the inhibition of the formation of the calcium/calmodulin complex. They are for example agents intervening at the level of the sarcoplasmic reticulum like for example dantrolene and TMB-8, calmodulin antagonists like for example phenothiazine, trifluoperazine, chlorpromazine or naphthalene derivative or local anaesthetics like dibucaine or dopamine antagonists like pimozide, haloperidol or calmidazolium.

Preferably, according to the invention agents active on the plasma membrane, inhibitors of the entry of calcium or also complexing calcium are used. Very preferably according to the invention the inhibitors of the entry of calcium such as alverine and/or its salts and/or its analogues and/or its derivatives are used.

Chloride Channel Agonists

II—The agents opening Cl⁻ channels such as described in U.S. Pat. Nos. 5,976,559 and 5,869,068 are also claimed as myorelaxing agents according to the invention.

In particular, they are benzodlazepines, GABA analogues, mimetic of the GABAergic receptor but also of glycine and/or their derivatives and all other substances which contribute to the opening of the Cl⁻ channel of the contractile cell and hence to an increase of cellular excitability by a significant increase of the membrane potential difference (ddp).

A composition according to the invention can also be characterized in that it contains both at least one calcium channel inhibitor and at least one chloride channel agonist.

The physiologically acceptable medium in which the compounds according to the invention can be used as well as its constituents, their quantity, the formulation of the composition and its method of preparation can be chosen by the specialist skilled in the art on the basis of his general knowledge as a function of the type of composition desired.

Generally speaking, this medium can be anhydrous or aqueous. Thus it may comprise an aqueous phase and/or a fatty phase, For an application to the skin, the composition may have the form in particular of an aqueous or oily solution; of a dispersion of the lotion or serum type; of emulsions of liquid or semi-liquid consistency of the milk type obtained by dispersion of a fatty phase in an aqueous phase (O/W) or the reverse (W/O); of suspensions or emulsions of soft consistency of the cream type or aqueous or anhydrous gels; of microcapsules or microparticles; vesicular dispersions of the ionic and/or non-ionic type.

For an application to the hair the composition may be in the form of aqueous, alcoholic or aqueous-alcoholic solutions; in the form of creams, gels, emulsions, foams; in the form of compositions for aerosol also comprising a propellant under pressure.

When the composition is available in aqueous form, in particular in the form of a dispersion, emulsion or aqueous solution, it can comprise an aqueous phase which may contain water, floral water and/or mineral water.

Said aqueous phase may comprise in addition alcohols such as $C_1$–$C_8$ monoalcohols and/or polyols such as glycerol, butyleneglycol, isoprene glycol, propylene glycol, polyethyleneglycol.

When the composition according to the invention is available in the form of an emulsion, it may optionally comprise in addition a surfactant, preferably in a quantity of 0.01 to 30% by weight compared with the total weight of the composition. The composition according to the invention may also comprise at least one coemulsifier which may be selected from oxyethylenated sorbitan monostearate, fatty alcohols such as stearyl alcohol or cetyl alcohol, or esters of fatty acids and polyols such as glyceryl stearate.

The composition according to the invention may also comprise a fatty phase, in particular constituted of fatty bodies liquid at 25° C., such as animal, vegetable, mineral or synthetic oils, volatile or not; fatty bodies solid at 25° C. such as waxes of animal, vegetable, mineral or synthetic origin; pasty fatty bodies; gums; their mixtures.

The volatile oils are usually oils with a saturating vapour pressure at least equal to 0.5 millibar (i.e. 50 Pa).

Of the constituents of the fatty phase mention may be made of:

the cyclic volatile silicones with 3 to 8, and preferably 4 to 6, silicon atoms.
the cyclocopolymers of the dimethylsiloxane/methylalkylsiloxane type,
the linear volatile silicones with from 2 to 9 silicon atoms
the hydrocarbon volatile oils, such as the isoparaffins and in particular isododecane and fluorinated oils.
the polyalkyl (C1–C20) siloxanes and in particular those with terminal trimethylsilyl groups, among which may be mentioned the linear polydimethylsiloxanes and the alkylmethylpolysiloxanes such as cetyldimethicone (designation CTFA),
the silicones modified by aliphatic and/or aromatic groups, optionally fluorinated, or by functional groups such as hydroxyl, thiol and/or amine groups.
the phenylated silicone oils,
the oils of animal, vegetable or mineral origin, and in particular the animal or vegetable oils formed by fatty acid esters and polyols, in particular the liquid triglycerides, for example the oils of sunflower, maize, soya, squash, grapeseed, sesame, hazelnut, apricot, almond or avocado; the fish oils, glycerol tricaprocaprylate, or the vegetable or animal oils of formula R1COOR2 in which R1 represents a higher fatty acid residue containing from 7 to 19 carbon atoms and R2 represents a branched hydrocarbon chain containing from 3 to 20 carbon atoms, for example Purcellin oil, paraffin oil, vaseline oil, perhydrosqualene, the oils of wheat germ, calophyllum, sesame, macadamia, grapeseed, colza, coconut, peanut, palm, castor oil, jojoba oil, olive oil or cereal germ oil; fatty acid esters; alcohols; acetylglycerides; octanoates, decanoates or ricinoleates of alcohols or polyalcohols; triglycerides of fatty acids; glycerides;
the fluorinated and perfluorinated oils
the silicone gums;
the waxes of animal, vegetable, mineral or synthetic origin such as the microcrystalline waxes, paraffin, petrolatum, vaseline, ozokerite, montan wax; beeswax, lanolin and its derivatives; candellila wax, ouricury wax, carnauba wax, Japan wax, cocoa butter, the waxes of cork fibres or sugar cane; the hydrogenated oils solid at 25° C., the ozokerites, the fatty esters and glycerides solid at 25° C.; the polyethylene waxes and the waxes obtained by Fischer-Tropsch synthesis; hydrogenated oils solid at 25° C.; lanolins; fatty esters solid at 25° C.; the silicone waxes; the fluorinated waxes.

In a known manner, the composition according to the invention may comprise the usual adjuvants in the field under consideration such as the hydrophilic or lipophilic gelling agents, hydrophilic or lipophilic additives, active compounds in particular cosmetic or pharmaceutical hydrophilic or lipophilic active agents, the preservatives, the antioxidants, the solvents, the perfumes, the fillers, the pigments, the pearlescent agents, the UV filters, the odour absorbers and the colouring matters. These adjuvants according to their nature may be introduced into the fatty phase, in the aqueous phase and/or in lipid microspheres.

The nature and the quantity of these adjuvants may be selected by the specialist skilled in the art on the basis of his general knowledge so as to obtain the desired form of presentation for the composition. In any case the specialist skilled in the art will take care to choose all of optional additional compounds and/or their quantity such that the advantageous properties of the composition according to the invention are not, or not substantially, impaired by the addition considered.

The cosmetic or pharmaceutical compositions according to the invention may be presented in particular in the form of a composition designed for the care and/or treatment of ulcerated areas or areas subjected to a cutaneous stress or microstress, in particular generated by exposure to UV and/or by being placed in contact with a irritant product.

Thus, the compositions according to the invention may be presented in particular in the form of:
- a product for the care, treatment, cleansing or protection of the skin of the face or body including the scalp, such as a care composition (daytime, nighttime, hydrating) for the face or body; an anti-wrinkle or anti-age composition for the face; a composition rendering the face mat; a composition for irritated skin; a composition for the removal of makeup; a milk for the body, in particular a hydrating milk, optionally after exposure to the sun;
- a sun protection composition, an artificial tanning composition (self-tanning) or care composition after exposure to the sun;
- a composition for the hair, and in particular a sun protection cream or gel; a care composition for the scalp, in particular against hair loss or stimulating hair growth; antiparasitic shampooing;
- a product for the make-up of the skin or the face, body or lips, such as foundation makeup, complexion cream, rouge or eyelid make-up, a free or compact powder, anti-shadow stick, a camouflaging stick, a lipstick, a lip care composition;
- a product for buccal hygiene such as toothpaste or a mouthwash.

The compositions according to the invention find a preferred application as care composition of the facial skin, of the anti-wrinkle or anti-age type, and as composition for sun protection or after sun.

The object of the present invention is also a cosmetic treatment method for the skin of the body or face, including the scalp, in which a cosmetic composition containing a combination of a compound of the N-acylamino-amide family and at least one calcium channel inhibitor or at least one chloride channel agonist is applied to the skin, left in contact then optionally rinsed.

The cosmetic treatment method of the invention may be used in particular by applying the cosmetic compositions such as defined above according to the usual procedure for the use of these compositions. For example: application of creams, gels, serums, lotions, make-up removal milks or anti-sun compositions to the skin or the dry hair; application of a lotion for the scalp to wet hair; application of toothpaste to the gums.

The object of the invention is also a cosmetic treatment method for wrinkles and/or skin creases consisting of applying to the skin a cosmetic composition comprising in a cosmetically acceptable medium an efficacious quantity of at least one inhibitor of at least one calcium channel.

By cosmetically acceptable medium is meant a medium compatible with the skin, the scalp and/or the mucous membranes.

The cosmetic treatment method of the invention can be used in particular by applying the cosmetic composition such as defined above according to the procedure usually used for these compositions. For example: application of creams, gels, serums, lotions, milks for the removal of make-up or anti-sun compositions to the skin or spray compositions.

The invention is illustrated in more detail in the following examples.

EXAMPLE 1

Preparation of {2-[acetyl-(3-trifluoromethyl-phenyl)-amino]-3-methyl-butyrylamino}ethyl acetate of the formula:

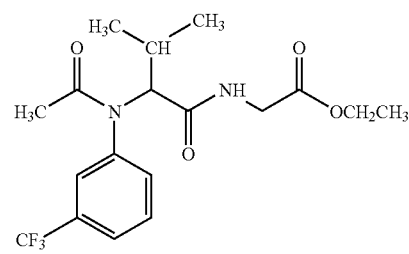

0.63 ml of isobutyraldehyde and 1 ml of trifluoromethylamine (1.15 eq) are mixed in 15 ml of methanol with stirring. The mixture is left to react for 15 minutes at 20° C., then 0.46 ml of acetic acid (1.15 eq) is added and the mixture is allowed to react for 10 minutes at 20° C. Then 0.8 ml of 95% ethyl isocyanoacetate (1 eq) is added and reaction is allowed to proceed for 48 hours at 20° C.

The reaction mixture is concentrated at the rotory evaporator and the residue is purified on a column of silica (eluant: heptane: 3/ethyl acetate: 7; Rf=0.5). 2.45 g of compound are obtained in the form of a waxy solid, hence in a yield of 91%.

$^1$H NMR (200 MHz; CDCl3) δ ppm: 0.9 (6H;q), 1.3 (3H;t), 1.8 (3H;s), 2.3 (1H;m), 4.0 (2H,q), 4.2 (2H;q), 4.4 (2H;d), 7.3 (1H;t), 7.5 (4H;m)

EXAMPLE 2

Preparation of {2-[acetyl-(3-trifluoromethyl-phenyl)-amino]-3-methyl-butyrylamino}acetic acid of the formula:

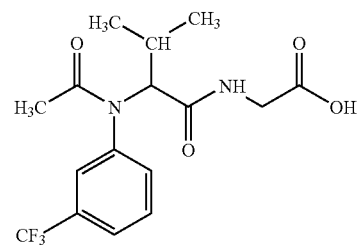

2 g of the compound prepared in Example 1 are dissolved in 30 ml of acetone. 30 ml of 2N sodium hydroxide are added and reaction is allowed to proceed for 6 hours at 20° C. The reaction mixture is concentrated at the rotory evaporator. The residual aqueous phase is acidified to pH 2 by the addition of concentrated HCl and extracted with CH2Cl2.

The organic phase is concentrated to dryness after being dried over sodium sulfate.

A residue is obtained which is dissolved in a mixture of basic water containing 10% ethanol, then acidified again to pH2 with concentrated HCl. The solution is extracted again with CH2Cl2 and the organic phase is dried over sodium sulfate. It is filtered and concentrated to dryness under vacuum in a rotory evaporator.

1.3 g of compound are obtained in the form of a slightly light brown solid in a yield of 70%.

$^1$H NMR (200 MHz; DMSO) δ ppm: 0.9 (6H;q), 3.7 (2H;m), 1.8 (4H;m), 4.8 (2H;d), 7.6 (4H;m), 8.4 (1H;t), 12.5 (1H;s)

EXAMPLE 3

The anti-elastase activity of compounds according to the invention was determined in vitro against human leukocyte elastase (HLE)

The test was performed in the following manner:

A substrate Me-OSAAPV-p-NA (methyl-O-succinate alanine alanine proline valine-p-nitroanilide) to which is added the HLE (40 milliunits per ml) and 0.1% of the test compound is incubated at 37° C. for 60 minutes.

The % of inhibition of the elastase activity tested is then determined by spectrophotometry.

The following compounds were tested:
Compound A: {2-[acetyl-(3-trifluoromethyl-phenyl)-amino]-3-methyl-butyrylamino}acetic acid
Compound B: (2-{benzyl-[(diethoxy-phosphoryl)-acetyl]-amino}-3-methyl-butyrylamino) ethyl acetate
Compound C: [2-(acetyl-benzyl-amino)-3-methyl-butyrylamino]acetic acid
Compound D: [2-(acetyl-benzyl-amino)-3-methyl-butyrylamino]ethyl acetate The following results were obtained:

| Compound (concentration: 0.1%) | % inhibition of elastase activity tested |
|---|---|
| Compound A | 67% |
| Compound B | 17% |
| Compound C | 20% |
| Compound D | 13% |

In the same manner the % of inhibition of the control elastase activity was determined for the compound A at different concentrations The following results were obtained:

| Concentration of compound A | % inhibition of elastase activity tested |
|---|---|
| 0.01% | 53% |
| 0.05% | 50% |
| 0.1% | 68% |
| 0.2% | 68% |

The compound A thus causes a strong inhibition of the elastase activity, even at low concentration.

EXAMPLE 4

The ex vivo activity of the compound of Example 2 was evaluated on surviving human skins treated with human leukocyte elastase (HLE).

The test is performed in the following manner:

Fresh sections of human skins derived from 2 different donors are treated for 2 hours at 20° C. with 20 μl of buffer solution (pH 7.4) containing optionally 10 μg/ml of HLE and optionally 0.1% of the test compound, optionally previously dissolved in ethanol.

The elastin fibres are stained blue with (+) catechol and quantified morphometrically by computer-assisted image analysis. The percentage of mean dermal surface occupied by the elastin fibres is thus evaluated The following results are obtained;

| | % surface occupied by elastin fibres | |
|---|---|---|
| | Skin 1 | Skin 2 |
| Control (untreated skin) | 12.7% | 15.25% |
| Skin treated with HLE | 4.85% | 6.85% |
| Skin treated with HLE + compound of example 2 | 13.95% | 11.85% |

Hence it is observed that the compound according to the invention generates a significant protection of the skins to destruction of the elastin fibres induced by elastase.

EXAMPLE 5

The ex vivo activity of the compound of Example 2 was evaluated on surviving human skins treated with human leukocyte elastase (HLE).

The test was performed in the following manner:

Fragments of normal human skin derived from three different donors are deposited in inserts placed in culture wells. Culture medium supplemented with antibiotics is added to the bottom of the wells. Passage by slow diffusion occurs between the two compartments through the intermediary of a porous membrane (pore size: 12 μm).

The culture medium is renewed every three days.

Optionally 0.5 μg of HLE per ml of culture medium is added to the skin fragments.

5 μl of test compound previously dissolved at 0.2% by weight in ethanol are also added every two days.

The skins are maintained in survival for 10 days at 37° C.,

The elastin fibres are stained blue with (+) catechol and quantified morphometrically by computer-assisted image analysis. The mean percentage dermal surface area occupied by the elastin fibres was thus evaluated.

The following results were obtained:

| | % surface occupied by elastin fibres |
|---|---|
| Control (untreated skin) | 7.4% |
| Skin treated with HLE | 5.1% |
| Skin treated with HLE + compound of example 2 | 7.1% |

Thus it was observed that the compound according to the invention generates a significant protection of the skins to the destruction of the elastin fibres induced by elastase.

EXAMPLE 6

The activity of the compound of Example 2 was evaluated on irradiated surviving human skins irradiated by UVA (8 J/cm2).

The test is performed in the following manner:

Fragments of normal human skin derived from four different donors are deposited in inserts placed in culture wells. Culture medium supplemented with antibiotics is added to the bottom of the wells. Passage by slow diffusion occurs between the two compartments through the intermediary of a porous membrane (pore size: 12 µm).

The culture medium is renewed every three days.

Every two days 5 µl of the test compound previously dissolved at 0.2% in ethanol are added to the skin fragments.

The skins are maintained in survival for 7 days at 37° C.

The skins are irradiated once only at 8 J/cm2 (Vilbert-Lourmat RMX-3W lamp).

The elastin fibres are stained blue with (+) catechol and quantified morphometrically by computer-assisted image analysis. The mean percentage dermal surface area occupied by the elastin fibres was thus evaluated.

The following results were obtained:

|  | Morphometric analysis of elastin fibres (superficial dermis) | Morphometric analysis of collagen (superficial dermis) |
| --- | --- | --- |
| Untreated skin | 6.75% | 87% |
| Skin treated by UVA (8 J/cm$^2$) | 3.9% | 81% |
| Skin treated by UVA (8 J/cm$^2$) + compound | 6.8% | 92% |

It is observed that the compound according to the invention has indeed an activity against the degradation of the elastin fibres in the superficial dermis of the skins irradiated by UVA.

This compound also has an adequate effect on the protection of collagen.

EXAMPLE 7

Composition for Topical Application

The following emulsion is prepared conventionally (% by weight):

| compound of Example 2 | 1% |
| --- | --- |
| Diazepam | 0.1% |
| propylene glycol isostearate | 13% |
| polyethylene glycol (8 OE) | 5% |
| propylene glycol | 3% |
| pentylene glycol | 3% |
| glyceryl stearate and polyethylene glycol stearate (100 OE) | 5% |
| oxyethylenated sorbitan monostearate (20 OE) | 0.5% |
| oxyethylenated (20 OE) oxypropylenated (5 OP) cetyl alcohol | 1% |
| gelling agents | 0.5% |
| C$_{12-15}$ alkyl benzoates | 4% |
| ethanol | 3% |
| sodium hydroxide | 0.12% |
| preservatives | qs |
| water | qsp 100% |

EXAMPLE 8

Face Cream

The following oil-in-water emulsion is prepared conventionally (% by weight):

| Compound of Example 2 | 1% |
| --- | --- |
| Alverin | 2% |
| Glycerol stearate | 2% |
| Polysorbate 60 (Tween 60 ® sold by the ICI company) | 1% |
| stearic acid | 1.4% |
| Triethanolamine | 0.7% |
| Carbomer | 0.4% |
| Liquid fraction of karite butter | 12% |
| Perhydrosqualene | 12% |
| Antioxidant | qs |
| Perfume | qs |
| Preservative | qs |
| Water | qsp 100% |

EXAMPLE 9

Milk for the Face

The following milk is prepared conventionally (% by weight):

| Vaseline oil | 7% |
| --- | --- |
| Compound of Example 2 | 1% |
| Alverine | 2% |
| Manganese gluconate | 2% |
| Glycine | 5% |
| Glyceryl monostearate, polyethylene glycol stearate (100 OE) | 3% |
| Carboxyvinyl polymer | 0.4% |
| Stearyl alcohol | 0.7% |
| Soya proteins | 3% |
| NaOH | 0.4% |
| Preservative | qs |
| Water | qsp 100% |

EXAMPLE 10

Anti-hair Loss Lotion

The following lotion is prepared conventionally (% by weight):

| Compound of Example 2 | 1% |
| --- | --- |
| Alverine | 2% |
| propylene glycol | 23% |
| ethanol | 55% |
| Aminexil | 1.5% |
| Water | qsp 100% |

It is possible to apply this anti-hair loss lotion to the scalp of alopecic individuals.

The invention claimed is:

1. A cosmetic or dermatological composition comprising an N-acylaminoamide inhibitor of elastase and at least one myorelaxing agent, wherein the myorelaxing agent is at least one selected from the group consisting of a calcium channel inhibitor and a chloride channel agonist and wherein the N-acylaminoamide inhibitor of elastase is a compound of formula (I):

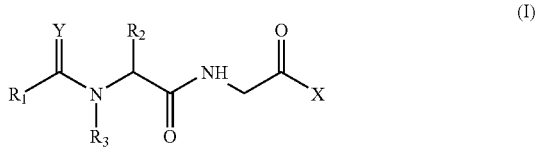

in which:
the Y radical represents O or S
the R1 radical represents:
(i) a hydrogen atom
(ii) a hydrocarbon radical, linear, branched or cyclic, saturated or unsaturated, containing from 1 to 18 carbon atoms, optionally substituted by 1 to 5 groups, identical or different, selected from the group consisting of
OH; —OR; —O—COR; —SH; —SR; —S—COR; —NH$_2$; —NHR; —NRR'; —NH—COR; -Hal (halogen); —CN; —COOR; —COR; —P(O)—(OR)$_2$; and —SO$_2$—OR;
with R and R' each representing independently a hydrocarbon radical, linear, branched or cyclic, saturated or unsaturated, containing 1 to 6 carbon atoms, optionally halogenated, said R and R' radicals being capable of forming together with N a 5- or 6- membered carbon ring that may include in addition at least one heteroatom selected from the group consisting of O, N and/or S in the ring, and/or may be substituted by 1 to 5 groups, identical or different, selected from the group consisting of
—OH; —OR"; —O—COR"; —SH; —SR"; —S—COR"; —NH$_2$; —NHR"; —NH—COR"; -Hal (halogen); —CN; —COOR"; —COR"; with R" representing independently a hydrocarbon radical, linear, branched or cyclic, saturated or unsaturated, containing 1 to 6 carbon atoms, optionally halogenated,
(iii) a radical selected from the group consisting of the radicals —OR; —NH$_2$; —NHR; —NRR'; —NH—COR; —COOR; —COR;
with R and R' each representing independently a hydrocarbon radical, linear, branched or cyclic, saturated or unsaturated, containing 1 to 6 carbon atoms, optionally halogenated; said R and R' radicals being capable of forming together with N a 5- or 6- membered carbon ring that may include in addition at least one heteroatom selected from the group consisting of O, N and/or S in the ring, and/or may be substituted by 1 to 5 groups, identical or different, selected from the group consisting of
—OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated,
the radical R2 represents a hydrocarbon radical, linear, branched or cyclic saturated or unsaturated, containing 1 to 18 carbon atoms, optionally substituted by 1 to 5 groups, identical or different, selected from the group consisting of
—OH; —OR; —O—COR; —SH; —SR; —S—COR; —NH$_2$; —NHR; —NRR"; —NH—COR; -Hal (halogen); —CN; —COOR; and —COR;
with R and R' each representing independently a hydrocarbon radical, linear, branched or cyclic, saturated or unsaturated, containing 1 to 6 carbon atoms, optionally halogenated, said R and R' radicals being capable of forming together with N a 5- or 6- membered carbon ring that may include in addition at least one heteroatom selected from the group consisting of O, N and/or S in the ring, and/or may be substituted by 1 to 5 groups, identical or different, selected from the group consisting of
—OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated,
the radical R3 represents a radical selected from the group consisting of those of formula (II) or (III)

in which:
y is an integer included between 0 and 5, and y' is an integer included between 1 and 5;
A is a divalent hydrocarbon radical, linear, branched or cyclic, saturated or unsaturated, containing 1 to 18 carbon atoms, optionally substituted by 1 to 5 groups, identical or different, selected from the group consisting of
—OH; —OR; —O—COR; —SH; —SR; —S—COR; —NH$_2$; —NHR; —NRR'; —NH—COR; -Hal (halogen); —CN; —COOR; —COR; —NO$_2$; and —SO$_2$—OR;
with R and R' each representing independently a hydrocarbon radical, linear, branched or cyclic, saturated or unsaturated, containing 1 to 6 carbon atoms, optionally halogenated, said R and R' radicals being capable of forming together with N a 5- or 6- membered carbon ring that may include in addition at least one heteroatom selected from the group consisting of O, N and/or S in the ring, and/or may be substituted by 1 to 5 groups, identical or different, selected from the group consisting of
—OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated,
B is a hydrocarbon radical, linear, branched or cyclic, saturated or unsaturated, containing 1 to 18 carbon atoms, optionally substituted by 1 to 5 groups, identical or different, selected from the group consisting of
—OH; —OR; —O—COR; —SH; —SR; —S—COR; —NH$_2$; —NHR; —NRR'; —NH—COR; -Hal (halogen); —CN; —COOR; —COR; —NO$_2$; and —SO$_2$—OR;
with R and R' each representing independently a hydrocarbon radical, linear, branched or cyclic, saturated or unsaturated; containing 1 to 6 carbon atoms, optionally halogenated, said R and R' radicals being capable of forming together with N a 5- or 6- membered carbon ring that may include in addition at least one heteroatom selected from the group consisting of O, N and/or S in the ring, and/or may be substituted by 1 to 5 groups, identical or different, selected from the group consisting of —OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated, the radical X represents a radical selected from the group consisting of —OH; —OR$_4$, —NH$_2$, —NHR$_4$, —NR$_4$R$_5$, —SR$_4$, —COOR$_4$; and —COR$_4$;

with R$_4$ and R$_5$ each representing independently a hydrocarbon radical, linear, branched or cyclic, saturated or unsaturated, containing 1 to 6 carbon atoms, optionally substituted by 1 to 5 groups, identical or different, selected from the group consisting of —OH; —OR; —O—COR; —SH; —SR; —S—COR; —NH$_2$; —NHR; —NRR'; —NH—COR; -Hal (halogen); —CN; —COOR; and —COR;

with R and R' each representing independently a hydrocarbon radical, linear, branched or cyclic, saturated or unsaturated, containing 1 to 6 carbon atoms, optionally halogenated, said R and R' radicals being capable of forming together with N a 5- or 6- membered carbon ring that may include in addition at least one heteroatom selected from the group consisting of O, N and/or S in the ring, and/or may be substituted by 1 to 5 groups, identical or different, selected from the group consisting of —OH; —OR"; —O—COR"; —SH; —SR"; —S—COR"; —NH$_2$; —NHR"; —NH—COR"; -Hal (halogen); —CN; —COOR"; and —COR"; with R" representing a hydrocarbon radical, linear, branched or cyclic, saturated or unsaturated, containing 1 to 6 carbon atoms, optionally halogenated, said R$_4$ and R$_5$ radicals being capable of forming together with N a 5- or 6 membered carbon ring that may include in addition at least one heteroatom selected from the group consisting of O, N and/or S in the ring, and/or may be substituted by 1 to 5 groups, identical or different, selected from the group consisting of —OH; —OR"; —O—COR"; —SH; —SR"; —S—COR"; —NH$_2$; —NHR"; —NH—COR"; -Hal (halogen); —CN; —COOR"; —COR"; with R" representing a hydrocarbon radical, linear, branched or cyclic, saturated or unsaturated, containing 1 to 6 carbon atoms, optionally halogenated, its mineral or organic acid salts, its optical isomers, in isolated form or as a racemic mixture.

2. The composition according to claim 1 in which the compound of formula (I) is such that:

the radical Y represents oxygen, and/or the radical R$_1$ represents hydrogen or a hydrocarbon radical, linear or branched, saturated or unsaturated, containing 1 to 12, and in particular 1, 2, 3, 4, 5 or 6 carbon atoms, optionally substituted, and/or the substituents of R$_1$ are selected from the group consisting of —OH, —OR and/or —P(O)—(OR)$_2$ with R representing a hydrocarbon radical, linear, branched or cyclic, saturated or unsaturated, containing 1 to 6 carbon atoms, optionally halogenated, and/or the radical R2 represents a hydrocarbon radical, linear, branched or cyclic, saturated or unsaturated, containing 1 to 12, and in particular 1, 2, 3, 4, 5 or 6 carbon atoms, optionally substituted; and/or the substituents of R2 are selected from the group consisting of —OH and —OR with R representing a hydrocarbon radical, linear, branched or cyclic, saturated or unsaturated, containing 1 to 6 carbon atoms, optionally halogenated, and/or the radical R3 represents a radical of formula —C$_6$H$_{(5-y')}$—B$_{y'}$' for which y'=1, 2 or 3; or a radical of formula —A—C$_6$H$_{(5-y)}$—B$_y$ for which y=0, 1 or 2; and/or the radical A of R3 is a divalent hydrocarbon radical, linear or branched, saturated or unsaturated, containing 1 to 12 carbon atoms, optionally substituted; and/or the radical B of R3 is a hydrocarbon radical, linear or branched, saturated or unsaturated, containing 1 to 12 carbon atoms, optionally substituted; and/or the substituents of A and/or B are selected from the group consisting of -Hal (halogen); —CN; —COOR; —NO$_2$; —SO$_2$—OR; with R representing a hydrocarbon radical, linear, branched or cyclic, saturated or unsaturated, containing 1 to 6 carbon atoms, optionally halogenated, and/or the radical X represents a radical selected from the group consisting of —OH or OR$_4$ with R$_4$ representing a hydrocarbon radical, linear, cyclic or branched, saturated or unsaturated, containing 1 to 6 carbon atoms, optionally substituted;

the substituents of R4 of X are chosen from —OH and —OR with R representing a hydrocarbon radical, linear, branched or cyclic, saturated or unsaturated, containing 1 to 6 carbon atoms, optionally halogenated.

3. The composition according to claim 1, in which the compound of formula (I) is such that:

the radical R1 represents a methyl, ethyl, propyl or isopropyl radical, optionally substituted by an —OH or —P(O)—(OR)$_2$ group with R representing methyl, ethyl, propyl or isopropyl; and/or the radical R2 represents a methyl, ethyl, propyl, isopropyl, n-butyl, tert-butyl or isobutyl radical; and/or the radical R3 represents a group selected from the group consisting of one of the following formulae:

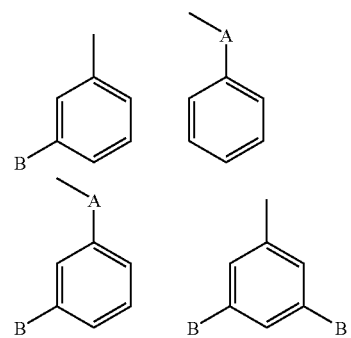

in which the divalent radical A is methylene, ethylene, propylene and/or the radical B is a methyl, ethyl, propyl or isopropyl radical substituted by one or more halogens, the radical X represents a radical selected from the group consisting of —OH, —OCH$_3$, —OC$_2$H$_5$, —OC$_3$H$_7$ or —OC$_4$H$_9$.

4. The composition according to claim 1, in which the compound of formula
(I) is selected from the group consisting of the following compounds:
{2-[acetyl-(3-trifluoromethyl-phenyl)-amino]-3-methyl-butyrylamino}acetic acid
{2-[acetyl-(3-trifluoromethyl-phenyl)-amino]-3-methyl-butyrylamino}ethyl acetate
[2-(acetyl-benzyl-amino)-3-methyl-butyrylamino]acetic acid
[2-(acetyl-benzyl-amino)-3-methyl-butyrylamino]ethyl acetate, and
(2-{benzyl-[(diethoxy-phosphoryl)-acetyl]-amino}-3-methyl-butyrylamino) ethyl acetate.

5. The composition according to claim 1, wherein the N-acylaminoamide elastase inhibitor is present in an amount of 0.00001 to 20% by weight of the total weight of the composition.

6. The composition according to claim 5, wherein the N-acylaminoamide elastase inhibitor is present in an amount of 0.001 and 10% by weight of the total weight of the composition.

7. The composition according to claim 5, wherein the N-acylaminoamide elastase inhibitor is present in an amount of 0.05 and 5% by weight.

8. The composition according to claim 1, wherein the myorelaxing agent is a calcium channel inhibitor selected from the group consisting of an inhibitor acting on the plasma membrane and an inhibitor acting intracellularly.

9. The composition according to claim 1, wherein the myorelaxing agent is a calcium channel inhibitor selected from the group consisting of Alverine, the organic and inorganic salts of Alverine, manganese, and the organic and inorganic salts of manganese.

10. The composition according to claim 1, wherein the myorelaxing agent is a calcium channel inhibitor selected from the group consisting of Alverine, manganese, and the organic and inorganic salts of manganese.

11. The composition according to claim 1, wherein the myorelaxing agent is a phenylalkylamine calcium channel inhibitor.

12. The composition according to claim 1, wherein the myorelaxing agent is a dihydropyridine calcium channel inhibitor.

13. The composition according to claim 1, wherein the myorelaxing agent is a calcium channel inhibitor selected from the group consisting of nifedipine, amlodipine, dazodipine, felodipine, isradipine, lanicardipine, nimodipine, nisoldipine, nitrendipine, and ryosidine.

14. The composition according to claim 1, wherein the myorelaxing agent is a benzothiazepine or diphenylpiperazine calcium channel inhibitor.

15. The composition according to claim 1, wherein the myorelaxing agent is a calcium channel inhibitor selected from the group consisting of diltiazem, cinnarizine, and flunarizine.

16. The composition according to claim 1, wherein the myorelaxing agent is a calcium channel inhibitor that intervenes at the level of the sarcoplasmic reticulum.

17. The composition according to claim 1, wherein the myorelaxing agent is a calcium channel inhibitor selected from the group consisting of dantrolene and TMB-8.

18. The composition according to claim 1, wherein the myorelaxing agent is a calcium channel inhibitor selected from the group consisting of phenothiazine, trifluoperazine, chlorpromazine and naphthalene.

19. The composition according to claim 1, wherein the myorelaxing agent is a calmodulin antagonist calcium channel inhibitor.

20. The composition according to claim 1, wherein the myorelaxing agent is a calcium channel inhibitor selected from the group consisting of local anesthetics and dopamine antagonists.

21. The composition according to claim 1, wherein the myorelaxing agent is a calcium channel inhibitor selected from the group consisting of dibucaine, pimozide, haloperidol and calmidazolium.

22. The composition according to claim 1, wherein the myorelaxing agent is a chloride channel agonist.

23. The composition according to claim 1, wherein the chloride channel agonist is selected from the group consisting of benzodiazepine, analogues of GABA, mimetic of the GABAergic receptor, and glycine.

24. The composition according to claim 1, comprising at least one calcium channel inhibitor myorelaxing agent and at least one chloride channel agonist myorelaxing agent.

25. The composition according to claim 1, comprising sufficient elastase inhibitor and myorelaxing agent to care for and/or treat ulcerated areas of the skin or areas of the skin subjected to a cutaneous stress or microstress.

26. A method of treating wrinkles and/or skin creases, comprising topically applying the composition of claim 1 to the skin.

27. The composition according to claim 1, wherein the myorelaxing agent is a calcium channel inhibitor selected from the group consisting of verapamil, anipamil, gallopamil; devapamil, falipamil, and tiapamil.

28. A method, comprising applying the composition of claim 1 to the skin, hair or mouth.

* * * * *